US00PP23829P3

(12) United States Plant Patent
Bijl

(10) Patent No.: US PP23,829 P3
(45) Date of Patent: Aug. 13, 2013

(54) ***NEPHROLEPIS* PLANT NAMED 'FLORIANE'**

(50) Latin Name: *Nephrolepis exaltata*
Varietal Denomination: Floriane

(75) Inventor: Jacob Bijl, Burgh-Haamstede (NL)

(73) Assignee: Vitro Plus B.V., Burgh Haamstede (NL)

( * ) Notice: Subject to any disclaimer, the term of this patent is extended or adjusted under 35 U.S.C. 154(b) by 187 days.

(21) Appl. No.: 13/065,604

(22) Filed: Mar. 24, 2011

(65) Prior Publication Data

US 2012/0246785 P1 Sep. 27, 2012

(51) Int. Cl.
*A01H 9/00* (2006.01)

(52) U.S. Cl.
USPC ..... Plt./379

(58) Field of Classification Search
USPC ..... Plt./379
See application file for complete search history.

*Primary Examiner* — June Hwu
*Assistant Examiner* — Louanne Krawczewicz Myers
(74) *Attorney, Agent, or Firm* — Cassandra Bright

(57) ABSTRACT

A new and distinct *Nephrolepis* cultivar named 'Floriane' is disclosed, characterized by a distinctive relaxed, nearly weeping plant habit, broad, nearly weeping foliage and overall broad plant habit. The near variety is a *Nephrolepis*, typically used for indoor ornamental purposes.

1 Drawing Sheet

Latin name of the genus and species: *Nephrolepis exaltata.* Variety denomination: 'FLORIANE'.

BACKGROUND OF THE INVENTION

The new cultivar was discovered as a naturally occurring, spontaneous whole plant mutation, among a commercial planting of *Nephrolepis exaltata* 'Montana' unpatented. 'Floriane' was discovered by the inventor, Jacob Johannes Bijl, a citizen of the Netherlands in October of 2009, at a commercial greenhouse in Zierikzee, The Netherlands.

Approximately 10 weeks after discovery of the interesting mutation, the inventor initiated cultivation in tissue culture, at a commercial laboratory in the Netherlands during December of 2009. Subsequently 'Floriane' has been asexually reproduced by micro-propagation in Burgh-Haamstede, The Netherlands and has shown that the unique features of this cultivar are stable and reproduced true to type through several generations.

SUMMARY OF THE INVENTION

The cultivar 'Floriane' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Floriane' These characteristics in combination distinguish 'Floriane' as a new and distinct *Nephrolepis* cultivar:

1. Distinctive, relaxed, nearly weeping, plant habit.
2. Broad foliage.
3. Broad plant habit.
4. Relaxed, nearly weeping foliage aspect.

COMPARISON TO PARENT

Plants of the new cultivar 'Floriane' are similar to plants of the parent; *Nephrolepis exaltata* 'Montana' in most horticultural characteristics, however, plants of the new cultivar 'Floriane' produces lighter green leaves than the parent variety. Additionally, the new variety produces more longer, broader leaves than 'Montana'. Leaves of 'Floriane' are more undulating on the margin, and have a more acute apex than 'Montana'. Additionally, the overall plant appearance is different, as leaves of 'Floriane' are more relaxed to almost weeping, whereas leaves of 'Montana' are held more upright.

COMMERCIAL COMPARISON

The most similar commercial *Nephrolepis exaltata* variety available to compare to 'Floriane' is *Nephrolepis exaltata* 'Ariane' U.S. Plant Pat. No. 21,218. Plants of 'Floriane' produce more leaves per plant than 'Ariane'. Additionally, 'Floriane' differs from 'Ariane' in having a less upright plant habit and less leaflets per leaf.

BRIEF DESCRIPTION OF THE PHOTOGRAPH

The accompanying photograph in FIG. 1 illustrates in full color a typical plant of 'Floriane' grown in a greenhouse. This plant is approximately 1 year old, shown in a 1.5 liter pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001, except where general terms of ordinary dictionary significance are used. The following observations and measurements describe 'Floriane' plants grown in a commercial greenhouse in the Netherlands, from February of 2010 through February of 2011. Temperatures were 18° C. at night and 22° C. during the day. Measurements and numerical values represent averages of typical plant types. No growth regulators or special treatments were used.

Botanical classification: *Nephrolepis exaltata* 'Floriane'.

PROPAGATION

Time to initiate roots.—Approximately 10 days at 23° C.

Time to produce a rooted plantlet.—Approximately 5 weeks at 20° C.

Root description: Very dense and freely branching, moderately fine, slightly fibrous, non-fleshy, colored near RHS Grey-Brown 199D.

PLANT

Growth habit: Broad, nearly weeping, indoor ornamental potted plant.

Plant shape: Flattened globular with arching, outwardly relaxed leaves.

Height: Approximately 29 cm in a 1.5 liter pot.

Plant spread: Approximately 90 cm.

Growth rate: Moderate to rapid.

Branching characteristics: Branches emerge directly from the roots.

Age of plant described: Approximately 12 months from a stage 3 tissue culture.

FOLIAGE

Frond:

*Quantity per plant*.—Average 250.

*Frond type*.—Compound pinnate. Pinnae per Frond: Average 102.

*Average frond length*(*including stipe*).—Approximately Pinnae 60.1 cm.

*Average frond width*.—Approximately 9.7 cm. Average Pinna Length: Approximately 5.8 cm. Average Pinna Width: At base approximately 1.7 cm. At mid-section approximately 1.3 cm.

*Pinna shape*.—Lanceolate to lanceolate-oblong. Pinna Apex: Obtuse. Pinna Base: Truncate.

*Overall frond shape*.—Narrow elliptic to narrow elliptic-oblong.

*Overall frond aspect*.—Arching.

Pinna:

*Margin*.—Crenate.

*Pinna aspect*.—Wavy.

*Texture of top surface*.—Smooth.

*Texture of bottom surface*.—Smooth.

*Appearance of top surface*.—Slightly glossy.

*Appearance of bottom surface*.—Slightly glossy.

*Pubescence*.—No pubescence of fronds or Pinnae.

*Color*.—Young foliage upper side: Near RHS Green 141B, tip near RHS Yellow-Green 144B. Young foliage under side: Color between RHS Green 143B and Yellow-Green 144A. Mature foliage upper side: Near RHS Green 137B. Mature foliage under side: Near RHS Green 137C.

*Venation*.—Type: Pinnate. Venation coloration upper side: Near RHS Yellow-Green 147A. Venation coloration under side: Near RHS Brown 200A.

Stipe:

*Length*.—Approximately 8.4 cm.

*Width*.—At geniculum: Approximately 2.5 cm. Above clump: Approximately 2.5 cm.

*Color*.—Upper side: Varies, either near RHS Green 143C or Yellow-Green 151A. Under side: Near RHS Brown 200D.

*Strength*.—Strong.

Rachis:

*Length*.—Average 43.7 cm.

*Diameter*.—Average 0.8 cm.

*Strength*.—Strong.

Pinna petiole: Pinnae are sessile.

Other foliage characteristics:

*Pinna rachis description*.—Rachis colored near Yellow-Green 144A on both sides; upper side of rachis moderately covered and under side sparsely covered with stellate hairs, average length: 1 mm, colored near RHS 197D.

FLOWER

Non-flowering variety.

OTHER CHARACTERISTICS

Spore production: Not detected to date.

Disease resistance: Neither resistance nor susceptibility to diseases or pests has been observed in this variety.

Temperature tolerance: Indoor tropical, hardy to at least USDA zone 10, tolerates high temperatures to at least 35° C.

Drought tolerance: No tolerance for drought.

What is claimed is:

1. A new and distinct cultivar of *Nephrolepis* plant named 'Floriane' as herein illustrated and described.

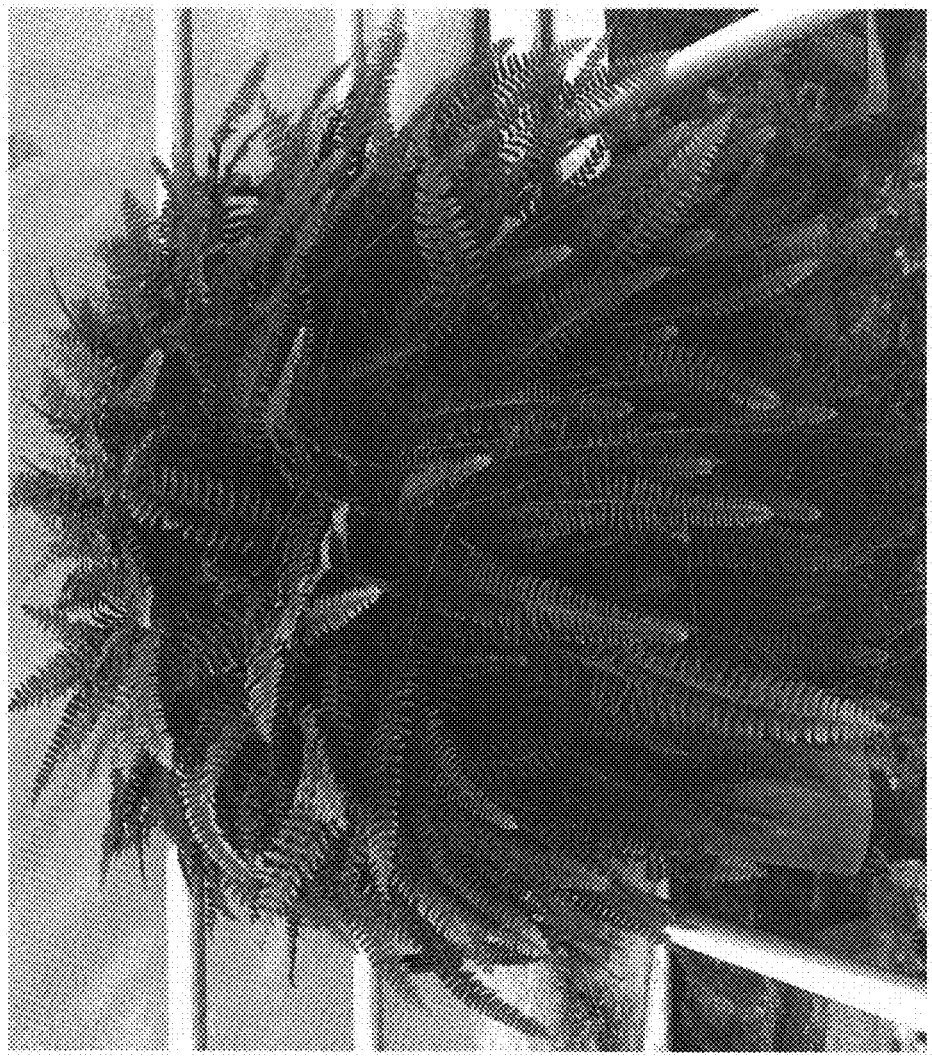

* * * * *